(12) United States Patent
Eichenseer et al.

(10) Patent No.: US 10,638,987 B2
(45) Date of Patent: May 5, 2020

(54) X-RAY DETECTOR WITH CORRECTION UNIT

(71) Applicant: Siemens Healthcare GmbH, Erlangen (DE)

(72) Inventors: Mario Eichenseer, Hirschaid (DE); Helmut Winkelmann, Eggolsheim (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 308 days.

(21) Appl. No.: 15/610,799

(22) Filed: Jun. 1, 2017

(65) Prior Publication Data
US 2017/0354389 A1    Dec. 14, 2017

(30) Foreign Application Priority Data

Jun. 8, 2016   (DE) .................... 10 2016 210 129

(51) Int. Cl.
*A61B 6/00*       (2006.01)
*G01T 1/00*       (2006.01)
(Continued)

(52) U.S. Cl.
CPC .............. *A61B 6/4266* (2013.01); *A61B 6/52* (2013.01); *G01T 1/00* (2013.01); *G01T 1/2018* (2013.01); *G01T 1/247* (2013.01); *H04N 5/217* (2013.01); *H04N 5/32* (2013.01); *H04N 5/357* (2013.01); *H04N 5/367* (2013.01); *H04N 5/3651* (2013.01); *A61B 6/4208* (2013.01); *A61B 6/54* (2013.01)

(58) Field of Classification Search
CPC ........... A61B 6/00; A61B 6/4266; A61B 6/52; A61B 6/54; A61B 6/58; A61B 6/5258; A61B 6/5205; A61B 6/5211; A61B 6/582; A61B 6/586; A61B 6/585
USPC ................................... 378/19, 207
See application file for complete search history.

(56) References Cited

U.S. PATENT DOCUMENTS

| 7,822,173 B2* | 10/2010 | Mattson | ................. | A61B 6/585 |
| | | | | 378/19 |
| 2002/0148968 A1 | 10/2002 | Der Haar | | |
| 2017/0020472 A1* | 1/2017 | Eusemann | ............. | A61B 6/032 |

FOREIGN PATENT DOCUMENTS

DE    10116222 A1    10/2002

OTHER PUBLICATIONS

Iampa, W. et al: "Multi-Module of X-Ray Array Detectors"; In; Proceedings of the International Symposium on Communications and Information Technologies 2008; pp. 547-550.
(Continued)

*Primary Examiner* — Jurie Yun
(74) *Attorney, Agent, or Firm* — Harness, Dickey & Pierce, P.L.C.

(57) ABSTRACT

An X-ray detector includes a detection unit to convert X-rays into a signal value and an evaluation unit. The detection unit and the evaluation unit are configured in a common component, the extent of the component along a first direction being not greater than the extent of the detection unit. The evaluation unit includes at least one correction unit to correct the signal values, a computation unit to control the correction, and a memory unit to store at least one correction parameter. The evaluation unit is designed such that the signal values are corrected as a function of the at least one correction parameter. A method and detector group are also disclosed.

18 Claims, 7 Drawing Sheets

(51) Int. Cl.
| | |
|---|---|
| *H04N 5/32* | (2006.01) |
| *H04N 5/365* | (2011.01) |
| *G01T 1/20* | (2006.01) |
| *H04N 5/357* | (2011.01) |
| *H04N 5/367* | (2011.01) |
| *G01T 1/24* | (2006.01) |
| *H04N 5/217* | (2011.01) |

(56) References Cited

OTHER PUBLICATIONS

German Office Action dated May 12, 2017.

\* cited by examiner

X-RAY DETECTOR WITH CORRECTION UNIT

PRIORITY STATEMENT

The present application hereby claims priority under 35 U.S.C. § 119 to German patent application number DE 102016210129.3 filed Jun. 8, 2016, the entire contents of which are hereby incorporated herein by reference.

FIELD

At least one embodiment of the invention generally relates to an X-ray detector, a detector group, a detector apparatus, a medical device and a use of the X-ray detector or detector group, wherein the X-ray detector comprises at least one correction unit.

BACKGROUND

In X-ray imaging, for example, in computer tomography, angiography or radiography, integrating indirectly-converting X-ray detectors or counting directly-converting X-ray detectors can be used.

The X-rays or the photons can be converted into light in indirectly-converting X-ray detectors using a suitable converter material, and into electric pulses, using photodiodes. Scintillators, for example, GOS ($Gd_2O_2S$), CsJ, YGO or LuTAG, are often used as a converter material. Scintillators are used in particular in medical X-ray imaging in the energy range up to 1 MeV. It is normal practice to use "indirectly-converting X-ray detectors", in which the conversion of the X-rays or gamma rays into electric signal values takes places in two steps. In a first step, the X-rays or gamma quants are absorbed in a scintillator element and converted into optically visible light, an effect known as luminescence. The light excited by luminescence is subsequently converted in a second step into an electric signal or a signal value by a first scintillator element that is optically coupled to a first photodiode. The signal value can be read out in digitalized form via an evaluation and readout electronics unit and subsequently forwarded to a system calculating unit.

The X-rays or photons can be converted into electric signals or pulses in directly-converting X-ray detectors using a suitable converter material. As converter materials, it is possible to use, for example, CdTe, CZT, CdZnTeSe, CdTeSe, CdMnTe, InP, TlBr2, HgI2, GaAs or others. The signals are evaluated by an evaluation unit, for example, an integrated circuit (Application Specific Integrated Circuit, ASIC). In counting X-ray detectors, incident X-rays are measured by counting the electric pulses that are triggered by the absorption of X-ray photons in the converter material. The height of the electric pulse is generally in proportion with the energy of the absorbed X-ray photon. As a result thereof, spectral information can be extracted by comparing the height of the electric pulse with a threshold value. The electric pulse can be converted into a signal value. Signal values can be read out and forwarded to the system computation unit.

An X-ray detector, in particular for use in a computer tomography unit, can consist of very many, for example, 1000 to 100,000, individual measurement channels, which generally operate simultaneously. Each measurement channel can comprise a collimation unit, a scintillator unit, a photodiode, a current/voltage converter, an analog-to-digital converter, and a computation unit with a plurality of steps. Typically, the collimation unit, the scintillator unit, the photodiode, the current/voltage converter, and the analog-to-digital converter are located in the detector system, that is, in the X-ray detector, in a detector group or in a detector apparatus. The computation unit is located outside the detector system, the signal values being forwarded by way of serial transmission, for example, in the Mbit/s or Gbit/s range, for example, to the system computation unit of the computer tomography unit.

The image quality or image impression can be improved by having a series of physical parameters, for example, the temperature coefficient or intensity linearity, operating homogeneously across the spatial extent or the course over time.

SUMMARY

The inventors have realized that the user's now high expectations in terms of image quality can currently no longer be achieved by simply making adequately high demands on the input material, for example, the converter material, or the conversion process. Instead, the whole manufacturing process has reached the border of what is technically feasible and ensures the quality of the end product by continual complex measurement of properties, sorting, and arranging items together. The inventors have realized that the latter additionally involves expensive storage.

Furthermore, the inventors have realized that by subdividing the detector apparatus into smaller units, known as modules or X-ray detectors, attempts are made to achieve high piece numbers and somewhat simpler components in order to then keep the quality high and the price low by way of higher piece effects and serial production.

The inventors have further realized that the end result of this production and optimization process is therefore subject, of course, to a distribution that is undesirable but unavoidable. By ultimate repair and/or sorting measures, rogue negative results can indeed be avoided, yet the real aim of delivering a predictable result within narrow tolerances has not yet been achieved in the current state of the art.

The inventors have also realized that each of the measurement channels comprises physically-caused deficiencies which can only be overcome by complex calibrations. These are time-consuming, sometimes computation-intensive and are also tied to the hardware used. Furthermore, the calibrations are generally not stable over a fairly long period and therefore have to be repeated regularly.

At least one embodiment of the invention includes an X-ray detector, a detector group, a detector apparatus, a medical device, and/or a use of the X-ray detector or of the detector group that allow a correction of the signal values directly in the X-ray detector or in the detector group.

At least one embodiment of the invention is directed to an X-ray detector; at least one embodiment of the invention is directed to a detector group; at least one embodiment of the invention is directed to a detector apparatus; at least one embodiment of the invention is directed to a medical device; and at least one embodiment of the invention is directed to a use of the X-ray detector or of the detector group.

At least one embodiment of the invention relates to an X-ray detector comprising a detection unit for converting X-rays into a signal value, and an evaluation unit. The detection unit and the evaluation unit are configured in a common component, wherein the extent of the component along a first direction is not greater than the extent of the detection unit. If the first direction runs in a curve, for example along the phi-direction in a computer tomography unit, the extent of the component along a first direction is not greater than the projection of the extent of the detection unit along the direction of propagation of the X-rays. The evaluation unit comprises at least one correction unit to correct the signal value, a computation unit to control the correction, and a memory unit to store at least one correction parameter. The evaluation unit is designed such that the signal value is corrected as a function of at least one correction parameter.

At least one embodiment of the invention further relates to a detector group comprising a plurality of X-ray detectors according to the invention. The detector group can also be referred to as a module group. A plurality of X-ray detectors can be arranged along the axis of rotation or along the curve of a detector apparatus along the rotation direction of the rotor. The X-ray detectors can preferably be arranged close beside one another, wherein the gap between adjacent X-ray detectors does not exceed, for example, the size of a detector element or of a few detector elements. Advantageously, a large detection area can be achieved.

At least one embodiment of the invention further relates to a detector apparatus comprising a plurality of detector groups according to at least one embodiment of the invention. The detector apparatus can advantageously be designed from easily interchangeable or exchangeable detector groups. Advantageously, a cost reduction is facilitated in production or in the event of repairs.

At least one embodiment of the invention further relates to a medical device comprising a detector apparatus according to at least one embodiment of the invention. The advantages of the X-ray detector according to at least one embodiment of the invention and the detector apparatus according to at least one embodiment of the invention can advantageously be transferred to the medical device. According to one embodiment of the invention, the medical device can be a computer tomography unit.

At least one embodiment of the invention further relates to a use of the X-ray detector according to at least one embodiment of the invention or of the detector group according to at least one embodiment of the invention for a method for the determination and correction of signal values comprising the steps: determination of signal values with the detection unit, offset correction of the signal values in the X-ray detector via an offset-correction unit, a computation unit and a memory unit, serialization via a serialization unit of the X-ray detector. The detection unit, the offset-correction unit, the computation unit, the memory unit and the serialization unit are configured in the X-ray detector. The determination of the signal value in the detection unit can denote the conversion of X-rays into an electric signal or a signal value. The advantages of the apparatus according to at least one embodiment of the invention can advantageously be transferred to the use of the X-ray detector according to at least one embodiment of the invention or of the detector group according to at least one embodiment of the invention. Advantageously, a method for correcting the offset in the X-ray detector can be carried out.

BRIEF DESCRIPTION OF THE DRAWINGS

Embodiments of the invention will be described in further detail hereinafter with the aid of the drawings, in which.

DETAILED DESCRIPTION OF THE EXAMPLE EMBODIMENTS

Figure 1:
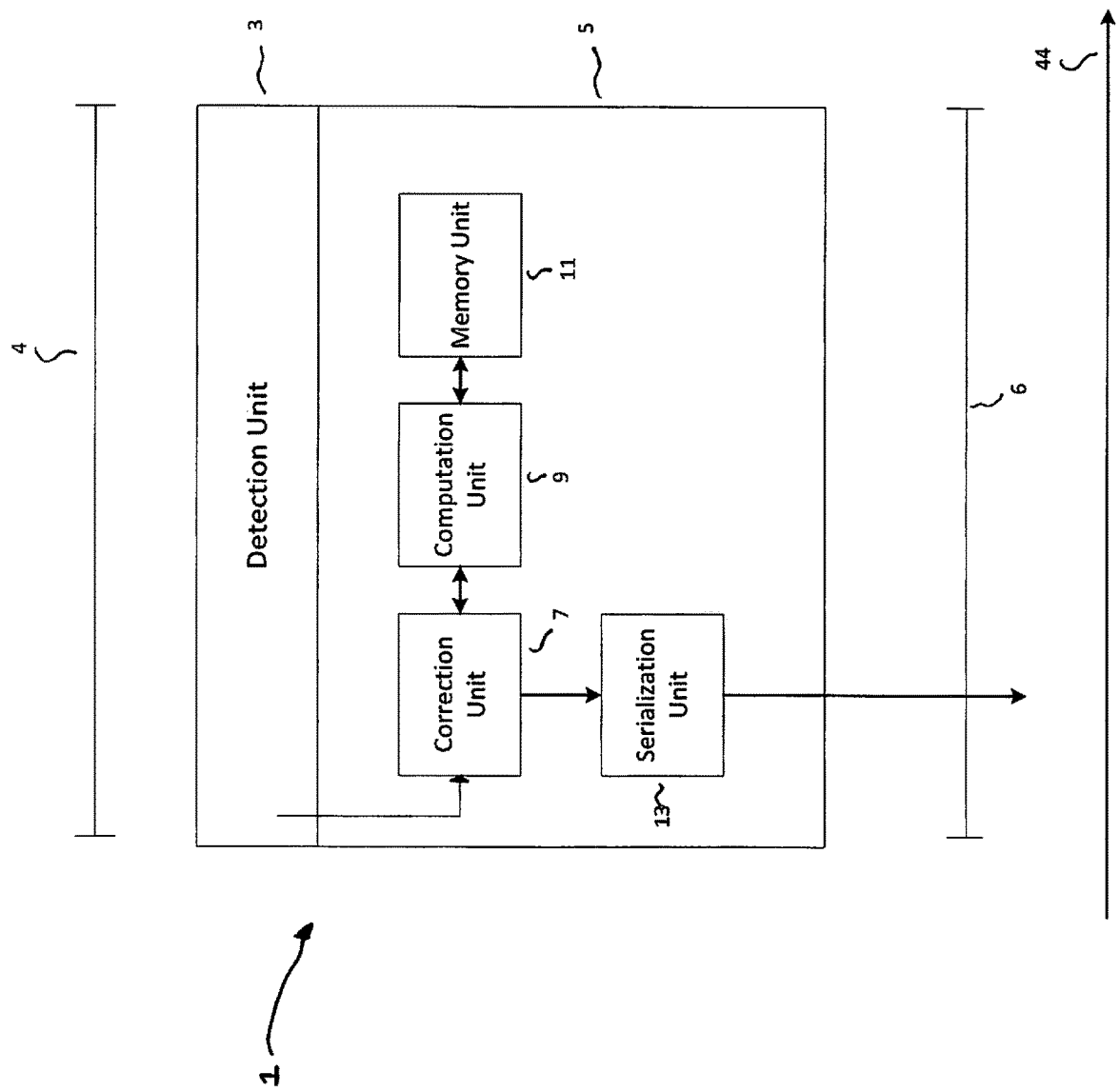
FIG. 1 shows in diagram form a concept for an X-ray detector according to a first embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s)

as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to an X-ray detector comprising a detection unit for converting X-rays into a signal value, and an evaluation unit. The detection unit and the evaluation unit are configured in a common component, wherein the extent of the component along a first direction is not greater than the extent of the detection unit. If the first direction runs in a curve, for example along the phi-direction in a computer tomography unit, the extent of the component along a first direction is not greater than the projection of the extent of the detection unit along the direction of propagation of the X-rays. The evaluation unit comprises at least one correction unit to correct the signal value, a computation unit to control the correction, and a memory unit to store at least one correction parameter. The evaluation unit is designed such that the signal value is corrected as a function of at least one correction parameter.

The X-ray detector can include a plurality of subunits. The X-ray detector can also be referred to as a detector module. The X-ray detector can be an indirectly-converting or a directly-converting X-ray detector. Preferably the X-ray detector can be an indirectly-converting detector. As a converter material, a scintillator, for example GOS ($Gd_2O_2S$), CsJ, YGO or LuTAG, can be used. The detection unit can comprise a converter element. In the case of an indirectly-converting detector, the detection unit can further comprise a photodiode. The X-ray detector can comprise a plurality of channels. Each channel can be assigned to a detector element or pixel. The channel can be assigned to a signal value. The evaluation unit can comprise evaluation or/and read-out-electronics, for example, an ASIC.

The detection unit and the evaluation unit, in at least one embodiment, are designed in a common component. The component can form a unit of the evaluation unit and detection unit. The evaluation unit can be indissolubly connected to the detection unit, for example, via a solder connection. Indissoluble can mean that the connection cannot be dissolved without causing any destruction. Indissoluble can mean that the connection does not comprise a reversible connection, for example, a plug connection.

Inside the component, the evaluation unit and the detection unit can alternatively be connected by a detachable connection, wherein they are in close proximity to each other, and the evaluation unit and the detection unit are located within a certain volume, in particular inside a rotor of a computer tomography unit or a detector apparatus or a detector group. For example, the component can be pushed or/and fixed into a detector bracket of the detector apparatus. The common component can be the entire X-ray detector. The detection unit and the evaluation unit can be arranged in a stacked arrangement. The evaluation unit can be arranged over the base area of the detection unit. The two-dimensional extent of the evaluation unit parallel to the two-dimensional extent of the detection unit or of the beam incidence area can be limited in a first direction, in the case of a computer tomography unit preferably in the phi-direction, that is, along the curve in the detector apparatus perpendicular to the axis of rotation z. The extent of the evaluation unit in the rotation direction can differ from the extent of the detection unit.

Advantageously, the two-dimensional extent of the evaluation unit in a first direction can be limited in order to be able to align X-ray detectors directly with each other and without any great gaps between them.

The correction unit can be designed to correct an offset, a gain, a drift or a linearity of the signal value or to correct an aging of the X-ray detector or to determine an irradiance of the X-ray detector, by which for example, the aging of the X-ray detector can be corrected.

Gain is the term used to denote the amplification factor of the signal or signal value. Drift is used to denote a change in the sensitivity of the converter material during or after irradiation of the X-ray detector with X-rays or also other electromagnetic radiation. The change in the sensitivity of the converter material can mean that different signal values are generated for an X-ray photon with the same energy in a first drift state and in a second drift state, the various signal values differing from one another more intensively than the quantum and electronics noise would lead one to expect.

In the case of an indirectly-converting converter material, the incident X-rays can be converted into more or less light due to a change in the sensitivity of the converter material. In the case of a directly-converting converter material, the change in the sensitivity of the converter material may bring about a change in the level of the electric pulse or a shift in the energy threshold.

Linearity can denote desired linear characteristics of the signal values at low and high signal values. Aging effects, for example changes in the sensitivity caused by radiation damage, can be corrected via the aging correction unit or a group aging correction unit.

Furthermore, an automatic detection of faulty channels can be configured by defining and applying failure criteria. The determination of the irradiance can mean that either the total of all the signals or signal values acquired or a dose is detected. From all the signal values that are acquired during the service life of the X-ray detector, a radiation history or aging history can be drawn up, describing the condition of the X-ray detector and any corrections or calibrations ensuing from the radiation history.

The computation unit can comprise a processor for the timing, monitoring/and or control of the X-ray detector. The computation unit can be a correction control unit.

Furthermore, the computation unit can be designed for timing or serialization of the signal values. The computation unit can be designed as an FPGA or microcontroller that can carry out the correction. The memory unit can comprise a permanent memory for production-dependent or time-varying data. The memory unit can permanently store correction parameters or the aging history or radiation history of the X-ray detector.

The inventors have realized that, as far as possible, all the electrical or electronic correction steps that bring about an equal performance of the individual channels can advantageously be carried out on the individual X-ray detectors or detector modules themselves. This means that both the individual correction algorithms and likewise the corresponding correction values are available directly in the evaluation unit, for example, on an electronics module of the X-ray detector. Specific corrections can be carried out relating to the X-ray detector itself and also corrections relating to adjacent X-ray detectors or specific corrections of the channels in the evaluation unit of the X-ray detector itself.

Advantageously, the scintillator production process can be simplified, wherein complex bundling or/and sorting of batch units with similar properties can be avoided or handled less strictly. Advantageously, the corrections and correction parameters can be determined irrespective of the target system and the exchange of X-ray detectors or components of the X-ray detector can be simplified; in particular it can be simplified by the adaptation that this allows to the momentary status or condition of the X-ray detector, in which a new X-ray detector is inserted. Advantageously, the correction, for example, an offset correction, a gain correction, a linearity correction, filtering or calibration can also be carried out outside the target system. Advantageously, the X-ray detectors can display a similarity in their imaging properties, the X-ray detectors being interchangeable in the manufacturing process, for example, and sorting according to imaging properties is not necessary.

The similarity with respect to drift or aging, for example, can be advantageously maintained during operation by corrections. Advantageously, an exchange can be simplified in the case of a replacement part. Advantageously, a recalibration of the target system, which is complex and in particular time-consuming, or the re-determination of correction parameters can be avoided. Advantageously, in the case of a rapid repair, wherein an X-ray detector or a detector module within a detector apparatus or a detector group is installed in a different position in the detector apparatus due to the lack of a replacement X-ray detector, complex calibrations or the complex determination of correction parameters in the system can be avoided and the system can soon be ready to use again. Advantageously, the maintenance costs for the medical device can be reduced by a rapid repair. Advantageously, the downstream computation effort in the system or medical device currently in operation can be minimized, it being possible to reduce the hardware demands on the reconstruction system of the medical device or to use capacities in addition to the reconstruction of the image from the signal values.

Advantageously, a detector-specific system calibration, that is, a calibration or correction of the X-ray detector in the system or in the medical device when installed can be avoided, as a result of which both the commissioning of a system can be accelerated and the software development effort necessary for this purpose, for example, the service software, can be reduced at the system end or in the reconstruction system. Advantageously, the X-ray detector can be used in various medical devices of a device type or can easily be exchanged. Advantageously, the development effort for other device types can be reduced. Advantageously, changes in the production of the X-ray detector due to a change of material, cost optimization or suchlike, for example, cannot affect the remainder of the system or medical device. Advantageously, a uniform interface can be provided with a defined performance or efficiency of the X-ray detector or detector group.

According to one embodiment of the X-ray detector according to the invention, the X-ray detector further comprises a serialization unit for serializing and/or sorting the signal values. The computation unit can include the serialization unit. The serialization unit can sort the data or signal values. The serialization unit can provide a data stream comprising a plurality of signal values. The serialization unit can comprise a plurality of bit-lines as an output. Advantageously, transmission to the reconstruction system or subsequent components can be simplified.

According to one embodiment of the X-ray detector according to the invention, the correction unit is an offset correction unit, a gain correction unit, a drift correction unit, an aging correction unit, a linearity correction unit, or a fault correction unit. The offset correction unit at least can be configured in the X-ray detector. The linearity correction unit can correct an intensity or a linearity of the X-ray detector or of the X-ray detector channel. The fault correction unit can detect faulty channels. The fault correction unit can interpolate signal values for faulty channels, for example, from the signal values for adjacent channels.

In at least one embodiment, the X-ray detector can comprise the following correction units in the following sequence: an offset correction unit, a gain correction unit, a drift correction unit, a linearity correction unit, an aging correction unit, and a fault correction unit. Advantageously, a necessary correction or a plurality of necessary corrections or all the necessary corrections can be carried out in the evaluation unit.

According to one embodiment of the X-ray detector according to the invention, the X-ray detector further comprises a determination unit to determine the irradiance. The irradiance can be a radiation intensity, an irradiated amount of energy, or a dose. Advantageously, by way of determining the irradiance over the service life, the aging of the X-ray detector can be determined.

At least one embodiment of the invention further relates to a detector group comprising a plurality of X-ray detectors according to the invention. The detector group can also be referred to as a module group. A plurality of X-ray detectors can be arranged along the axis of rotation or along the curve of a detector apparatus along the rotation direction of the rotor. The X-ray detectors can preferably be arranged close beside one another, wherein the gap between adjacent X-ray detectors does not exceed, for example, the size of a detector element or of a few detector elements. Advantageously, a large detection area can be achieved.

According to one embodiment of the detector group according to the invention, the detector group further comprises a detector group control for controlling the X-ray detectors, for data compression of the signal values or for correcting the signal values. The detector group control can also be a data concentrator, said data concentrator being able to reduce the data volume, for example, of the signal values. Advantageously, the signal values from the plurality of X-ray detectors can be combined in one data stream. Advantageously, the plurality of X-ray detectors can comprise a common detector group control.

According to one embodiment of the detector group according to the invention, the detector group further comprises a group gain correction unit, a group drift correction unit, a group aging correction unit, a group linearity correction unit, a group fault correction unit and/or a group determination unit to determine the irradiance. The group gain correction unit can carry out the gain correction for the plurality of X-ray detectors. The group drift correction unit can carry out the drift correction for the plurality of X-ray detectors. The group aging correction unit can carry out the aging correction for the plurality of X-ray detectors. The group linearity correction unit can carry out the linearity correction for the plurality of X-ray detectors. The group fault correction unit can carry out the correction of faulty detector elements for the plurality of X-ray detectors. The group determination unit can determine the irradiance for the plurality of X-ray detectors.

The X-ray detector can comprise at least one correction unit. Advantageously, the X-ray detector with the at least one correction unit can facilitate the further corrections in the group correction units, for example, a group gain correction unit, a group drift correction unit, a group aging correction unit, a group linearity correction unit, a group fault correction unit and/or a group determination unit to determine the irradiance. The X-ray detector can for example, comprise the determination unit to determine the irradiance, such that a correction of the drift and the aging can be carried out in the group drift correction unit and the group aging correction unit.

The X-ray detector can comprise correction parameters determined in the memory unit in the production process, for example, for correcting gain, linearity or the faulty channels. Advantageously, the computation effort in the X-ray detector or detector module can be reduced, wherein specific corrections can nevertheless be carried out in the X-ray detector itself. Advantageously, a reasonably priced variant of the detector group according to the invention can be produced.

A plurality of correction units can be implemented jointly for all the X-ray detectors in a computation unit of the detector group control. Advantageously, a reasonably priced variant of the detector group according to the invention can be produced. Advantageously, in faulty channels, an interpolation of the signal values above the limits of the X-ray detector can ensue. Advantageously, the detector group control can comprise a common computation unit, such that less powerful computation units can be configured or computation units with lower performance can be configured in the X-ray detectors. For example, in the detector apparatus the number of powerful computation units in combination with a plurality of correction units can be reduced by a factor of 10. Advantageously, the detector groups can be exchanged in the event of repairs, instead of having small sensitive X-ray detectors, such that the repair can be simplified.

According to one embodiment of the detector group according to the invention, the detector group further comprises a communications apparatus between X-ray detectors in the detector group. The communications apparatus can facilitate an interpolation of signal values from an X-ray detector and from an adjacent X-ray detector. The exchange of an X-ray detector can advantageously be simplified, since the downstream processing steps do not require any knowledge of the fault in a channel or of the interpolation of the signal value.

At least one embodiment of the invention further relates to a detector apparatus comprising a plurality of detector groups according to at least one embodiment of the invention. The detector apparatus can advantageously be designed from easily interchangeable or exchangeable detector groups. Advantageously, a cost reduction is facilitated in production or in the event of repairs.

At least one embodiment of the invention further relates to a medical device comprising a detector apparatus according to at least one embodiment of the invention. The advantages of the X-ray detector according to at least one embodiment of the invention and the detector apparatus according to at least one embodiment of the invention can advantageously be transferred to the medical device. According to one embodiment of the invention, the medical device can be a computer tomography unit.

At least one embodiment of the invention further relates to a use of the X-ray detector according to at least one embodiment of the invention or of the detector group according to at least one embodiment of the invention for a method for the determination and correction of signal values comprising the steps: determination of signal values with the detection unit, offset correction of the signal values in the X-ray detector via an offset-correction unit, a computation unit and a memory unit, serialization via a serialization unit of the X-ray detector. The detection unit, the offset-correction unit, the computation unit, the memory unit and the serialization unit are configured in the X-ray detector. The determination of the signal value in the detection unit can denote the conversion of X-rays into an electric signal or a signal value. The advantages of the apparatus according to at least one embodiment of the invention can advantageously be transferred to the use of the X-ray detector according to at least one embodiment of the invention or of the detector group according to at least one embodiment of the invention. Advantageously, a method for correcting the offset in the X-ray detector can be carried out.

According to one embodiment of the use according to the invention, the method further comprises at least one of the following steps: gain correction of the signal values via a gain correction unit or of a group gain correction unit, drift correction of the signal values via a drift correction unit or of a group drift correction unit, aging correction of the signal values via an aging correction unit or of a group aging correction unit, linearity correction of the signal values via a linearity correction unit or of a group linearity correction unit, and/or fault correction of the signal values via a fault correction unit or of a group fault correction unit. The corrections can be configured either in the X-ray detector or in the detector group control. Advantageously, the corrections can be carried out in the detector group. Advantageously, correction steps in the system computation unit can be avoided.

FIG. 1 shows an example of an embodiment of the X-ray detector according to the invention 1 as per a first embodiment. The X-ray detector 1 comprises a detection unit 3 for converting X-rays into a signal value, and an evaluation unit 5. The detection unit 3 can comprise a channel, for example. The X-rays can be converted by way of a directly-converting or indirectly-converting converter material in the detection unit 3 and the evaluation unit aligned therewith 5 into a signal value. The signal value is converted in the evaluation unit 5 into a digital signal value. The detection unit 3 and the evaluation unit 5 are configured in a common component, the extent 6 of the component along a first direction 44, in a computer tomography unit preferably in the phi-direction, not being greater than the extent 4 of the detection unit 3. The common component is the X-ray detector 1. The signal value is forwarded by the detection unit 3 to the evaluation unit 5.

The evaluation unit 5 comprises at least one correction unit 7 to correct the signal value, a computation unit 9 to control the correction, and a memory unit 11 to store at least one correction parameter. The computation unit 9 can further be designed for time-logging. The evaluation unit 5 is designed such that the signal value is corrected as a function of the at least one correction parameter. The signal value is corrected in the correction unit 7. The correction unit 7 is connected to a computation unit 9. The computation unit 9 is connected to a memory unit 11. The correction unit 7 is connected to a serialization unit 13, which provides an output signal.

Figure 2:
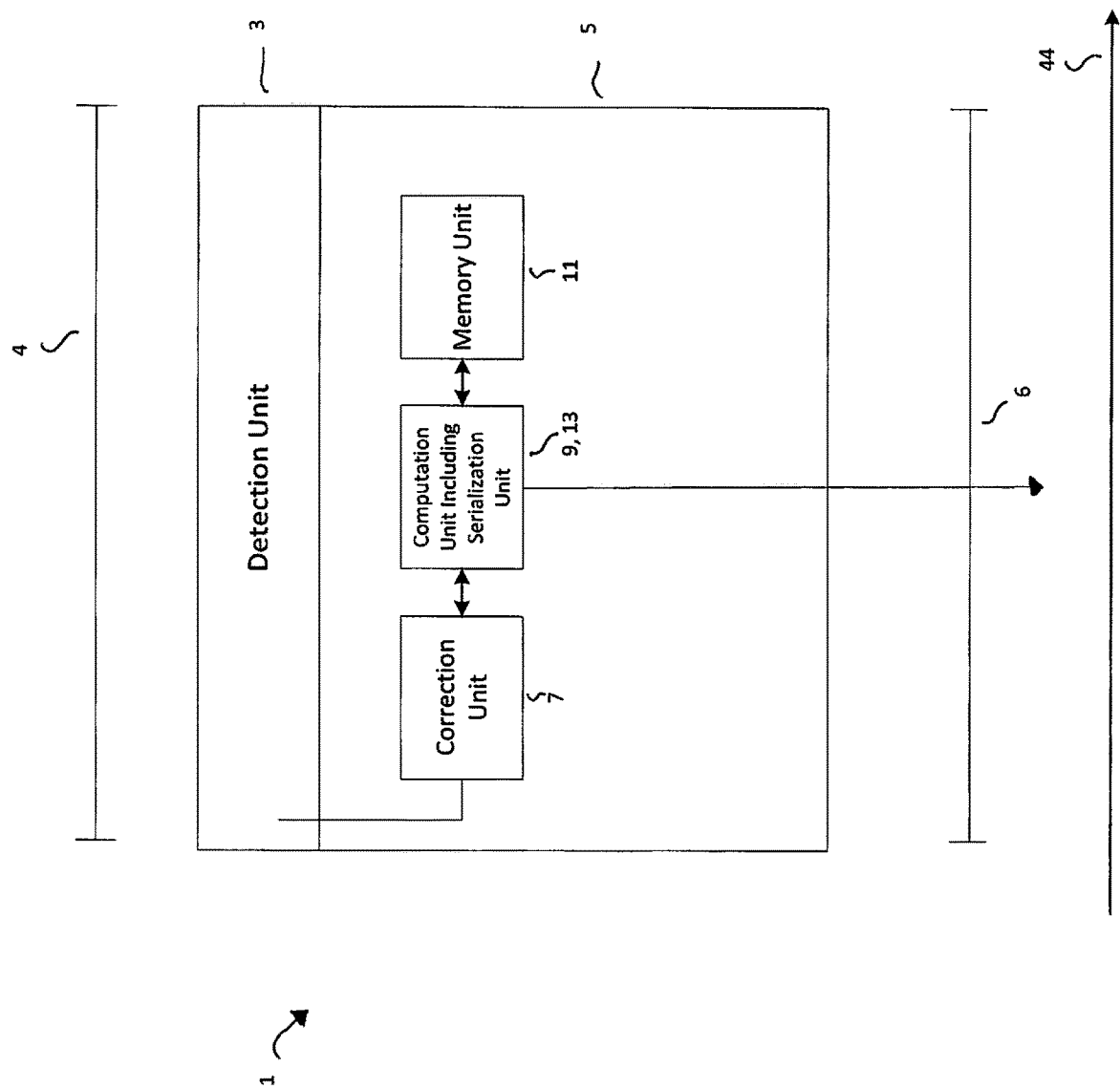
FIG. 2 shows in diagram form a concept for an X-ray detector according to a second embodiment of the invention.

FIG. 2 shows an example of a design of the X-ray detector according to the invention 1 as per a second embodiment. The correction unit 7 is connected to a computation unit 9, which comprises a serialization unit 13. The computation unit 9 is connected to the memory unit 11.

Figure 3:
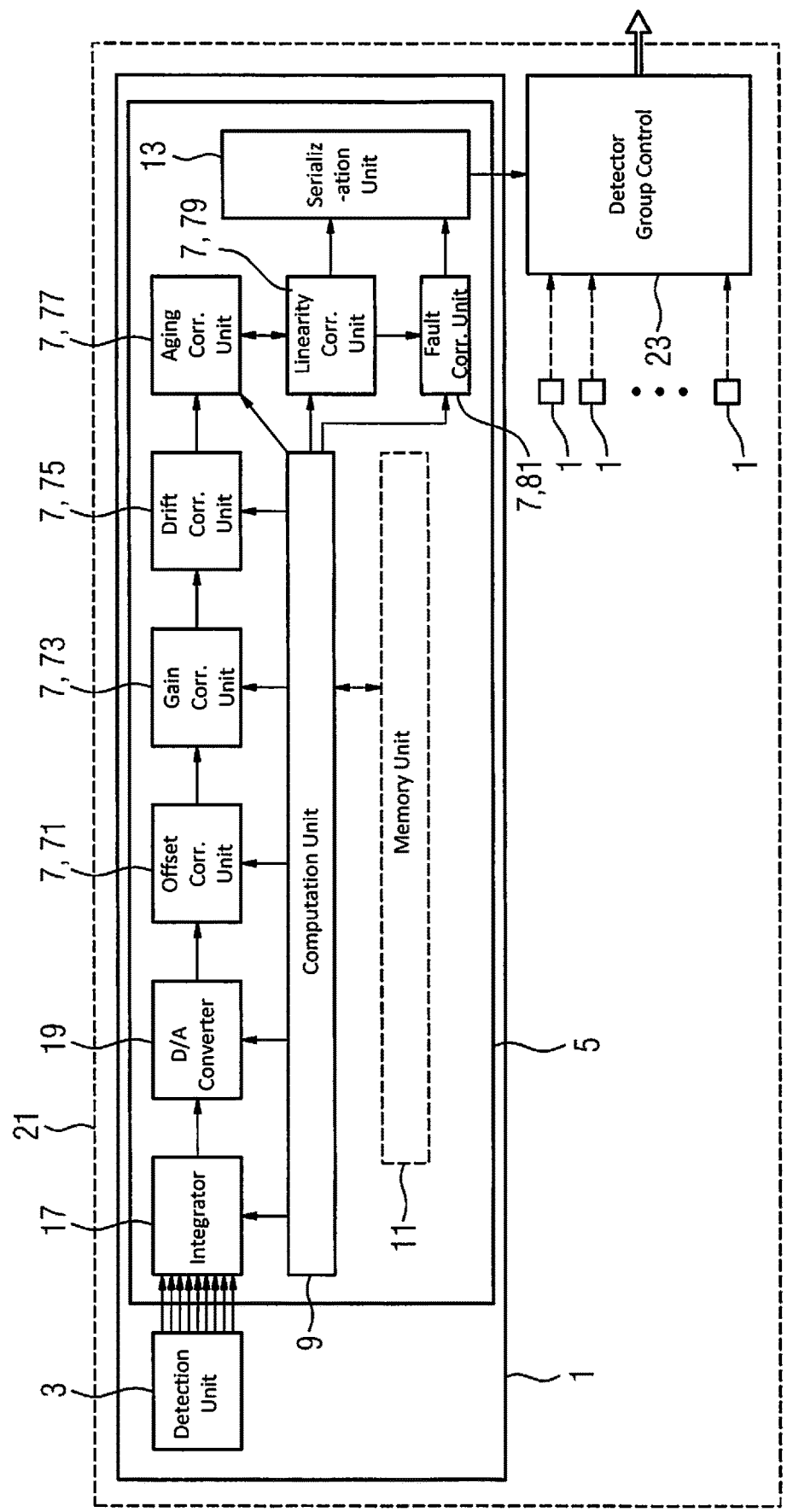
FIG. 3 shows in diagram form a concept for an X-ray detector group according to a first embodiment of the invention.

FIG. 3 shows an example of a design of the detector group according to the invention 21 as per a first embodiment. The detector group 21 comprises a plurality of X-ray detectors 1. The detector group 21 further comprises a detector group control 23 for controlling the X-ray detector 1, for data compression of the signal values or for correcting the signal values. The detection unit 3 comprises a plurality of channels, in FIG. 3 nine channels, for example. The signal value in the detection unit 3 is forwarded to the evaluation unit 5. The evaluation unit 5 comprises an integrator 17 and an analog-to-digital converter 19 as first steps in processing the signal value and to convert the signal value into a digital signal value. Subsequently, a plurality of correction units 7 are configured.

The evaluation unit 5 comprises an offset-correction unit 71, a gain correction unit 73, a drift correction unit 75, an aging correction unit 77, a linearity correction unit 79 and a fault correction unit 81, in which the signal value is corrected in stages. The computation unit 9 is connected to the integrator 17, to the digital-to-analog-converter 19, to the offset-correction unit 71, to the gain correction unit 73, to the drift correction unit 75, to the aging correction unit 77, to the linearity correction unit 79 and to the fault correction unit 81. The computation unit 9 is connected to the memory unit 11. In the memory unit 11, the X-ray detector 1 comprises correction parameters determined in the production process, for example, to correct the gain, the linearity or the faulty channels. The corrected signal value is further directed to the serialization unit 13, in which a plurality of signal values, for example the signal values from a plurality of channels, are sorted. The output signal from the serialization unit 13 is forwarded to the detector group control 23, in which the signal values from a plurality of X-ray detectors 1 are combined and forwarded to the system computation unit.

Figure 4:
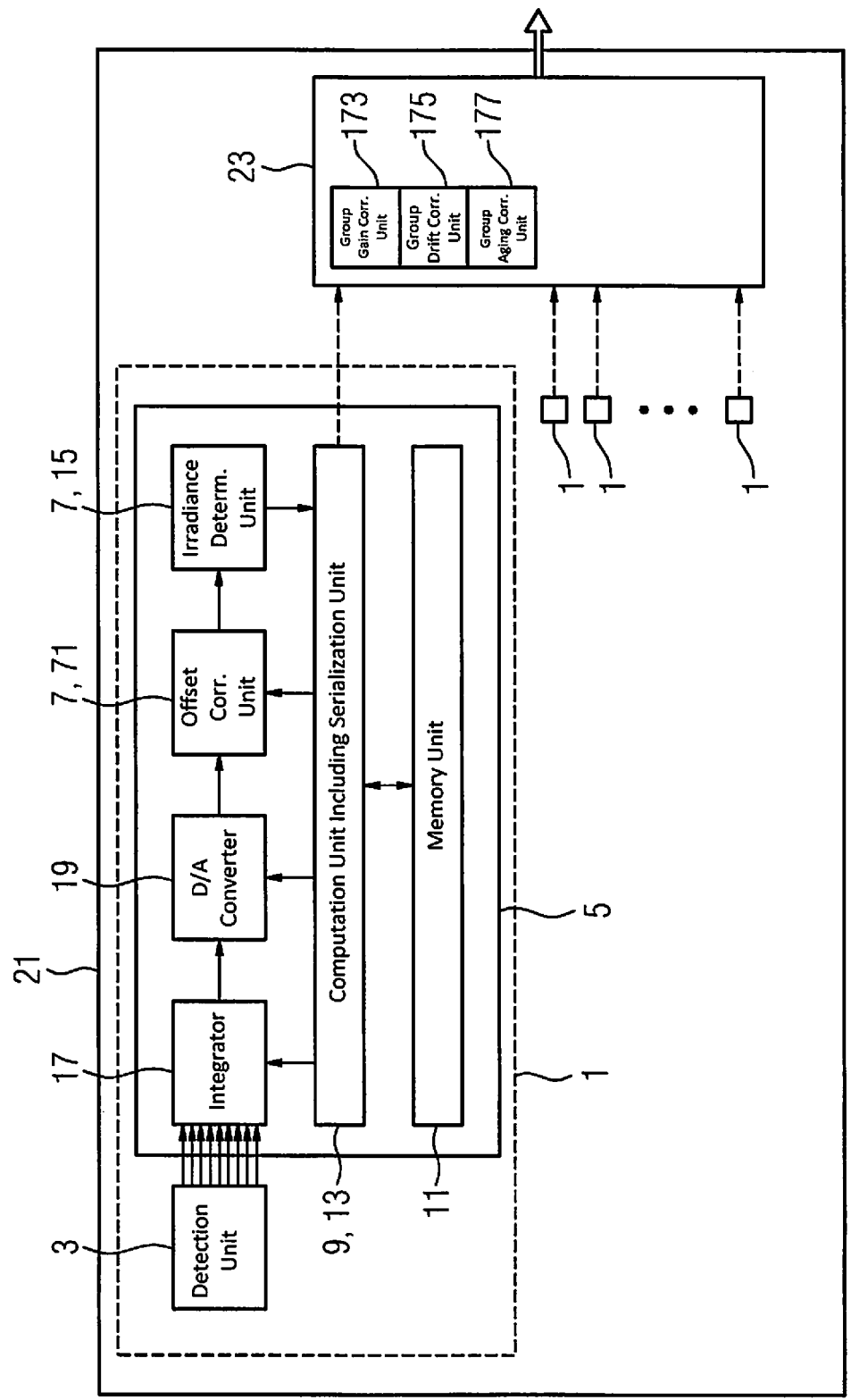
FIG. 4 shows in diagram form a concept for an X-ray detector group according to a second embodiment of the invention.

FIG. 4 shows an example of a design of the detector group according to the invention 21 as per a second embodiment. Connected to the digital-to-analog converter 19, the offset-correction unit 71 and the irradiance determination unit 15 are configured in the evaluation unit 5. The computation unit 9 is connected to the integrator 17, to the digital-to-analog-converter 19, to the offset-correction unit 71 and to the irradiance determination unit 15.

The computation unit 9 includes the serialization unit 13. The computation unit 9 is connected to the memory unit 11. The output signal from the computation unit 9 with the serialization unit 13 is forwarded to the detector group control 23.

The detector group control 23 can be designed as a data concentrator, that is, to reduce the data volume and also for pre-processing the signal values. The detector group control 23 further comprises the group gain correction unit 173, the group drift correction unit 175 and the group aging correction unit 177.

The group gain correction unit 173, the group drift correction unit 175, and the group aging correction unit 177 correct the signal values for the plurality of X-ray detectors 1. The correction parameters can be stored in a further memory unit of the detector group control 23.

Figure 5:
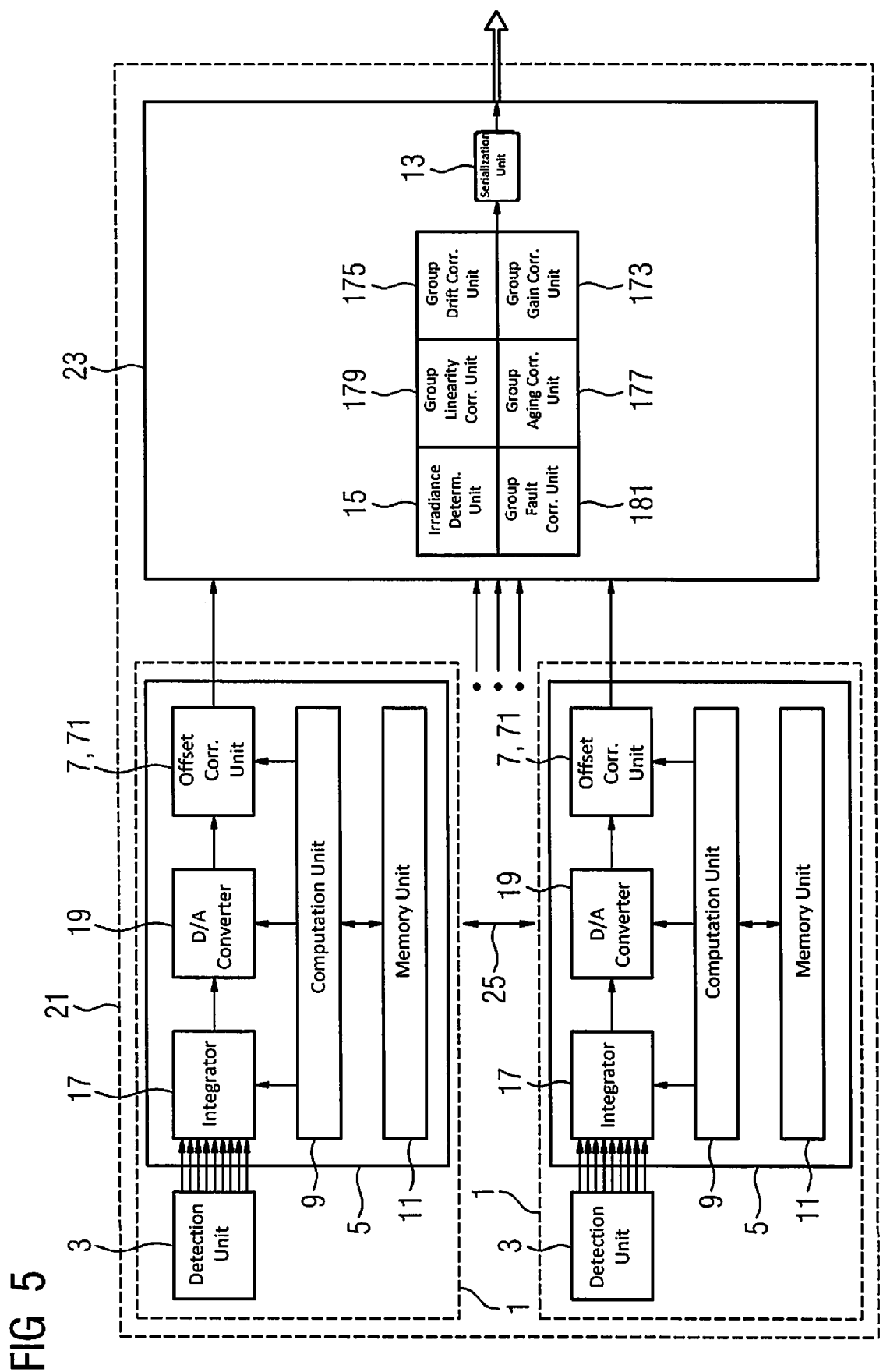
FIG. 5 shows in diagram form a concept for an X-ray detector group according to a third embodiment of the invention.

FIG. 5 shows an example of a design of the detector group according to the invention 21 as per a third embodiment. The evaluation unit 5 comprises an integrator 17 and an analog-to-digital converter 19. Connected to the digital-to-analog converter 19, the offset-correction unit 71 is configured in the evaluation unit. The computation unit 9 is connected to the integrator 17, to the digital-to-analog-converter 19 and to the offset-correction unit 71. The output signal from the offset-correction unit 71 is forwarded to the detector group control 23.

The detector group control 23 can be designed as a data concentrator, that is, to reduce the volume of data and also for pre-processing the signal values. The detector group control 23 further comprises the group gain correction unit 173, the group drift correction unit 175, the group aging correction unit 177, the group linearity correction unit 179 and the group fault correction unit 181. The detector group control 23 can comprise an irradiance determination unit 15, common to all the X-ray detectors 1.

A plurality of corrections can be carried out jointly for all the X-ray detectors 1 in a further computation unit in the detector group control 23. The detector group control 23 comprises a serialization unit 13 upstream of the output. Alternatively (not shown) the serialization unit 13 can be encompassed by the computation unit 9. A communications device 25 is configured between two, for example, adjacent, X-ray detectors 1.

Figure 6:
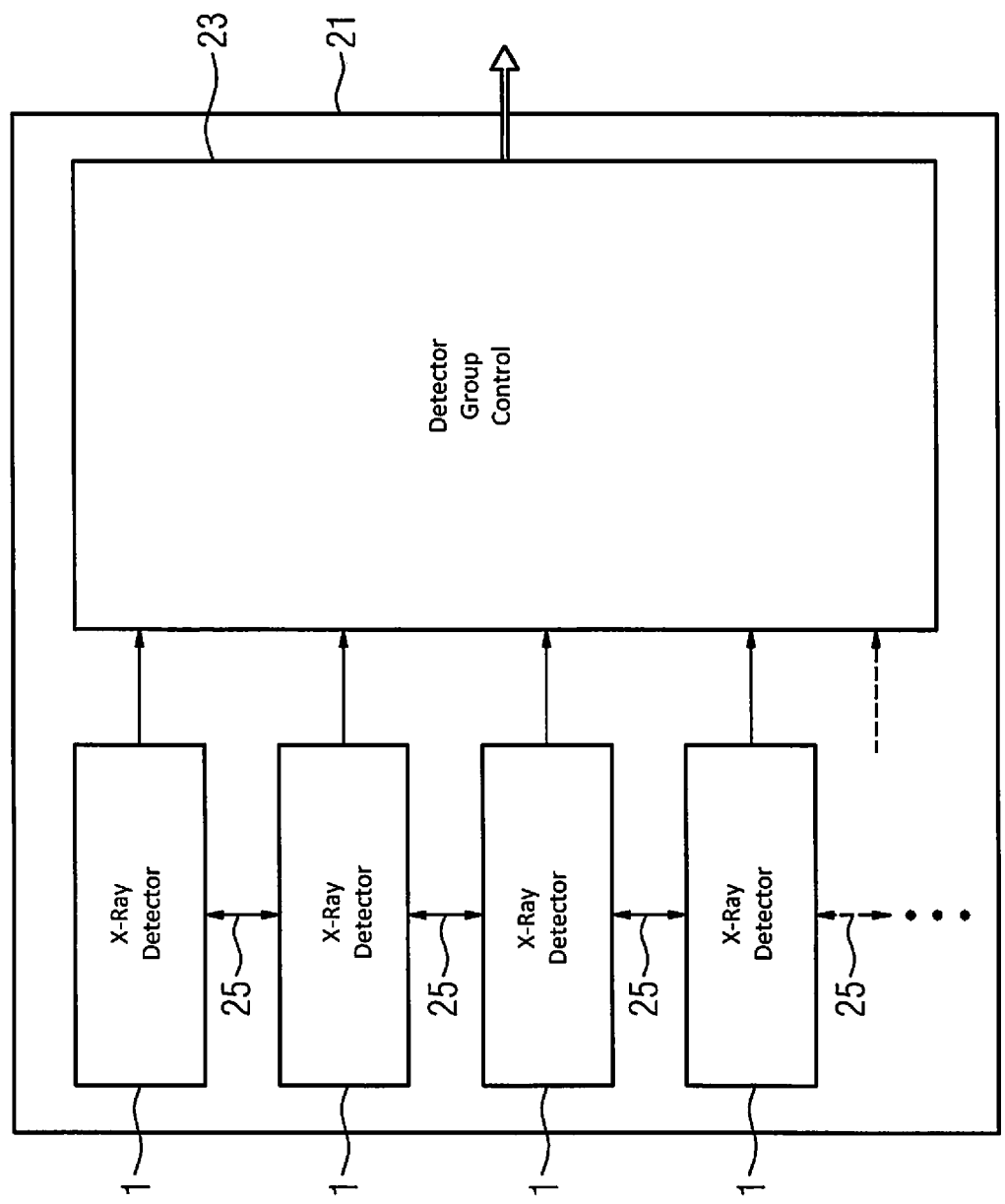
FIG. 6 shows in diagram form a concept for an X-ray detector group according to a fourth embodiment of the invention.

FIG. 6 shows an example of a design of the detector group according to the invention 21 as per a fourth embodiment. The adjacent X-ray detectors 1 are connected to a communications apparatus 25. The communications apparatus 25 allows an interpolation of signal values from an X-ray detector 1 and from an adjacent X-ray detector 1.

Figure 7:
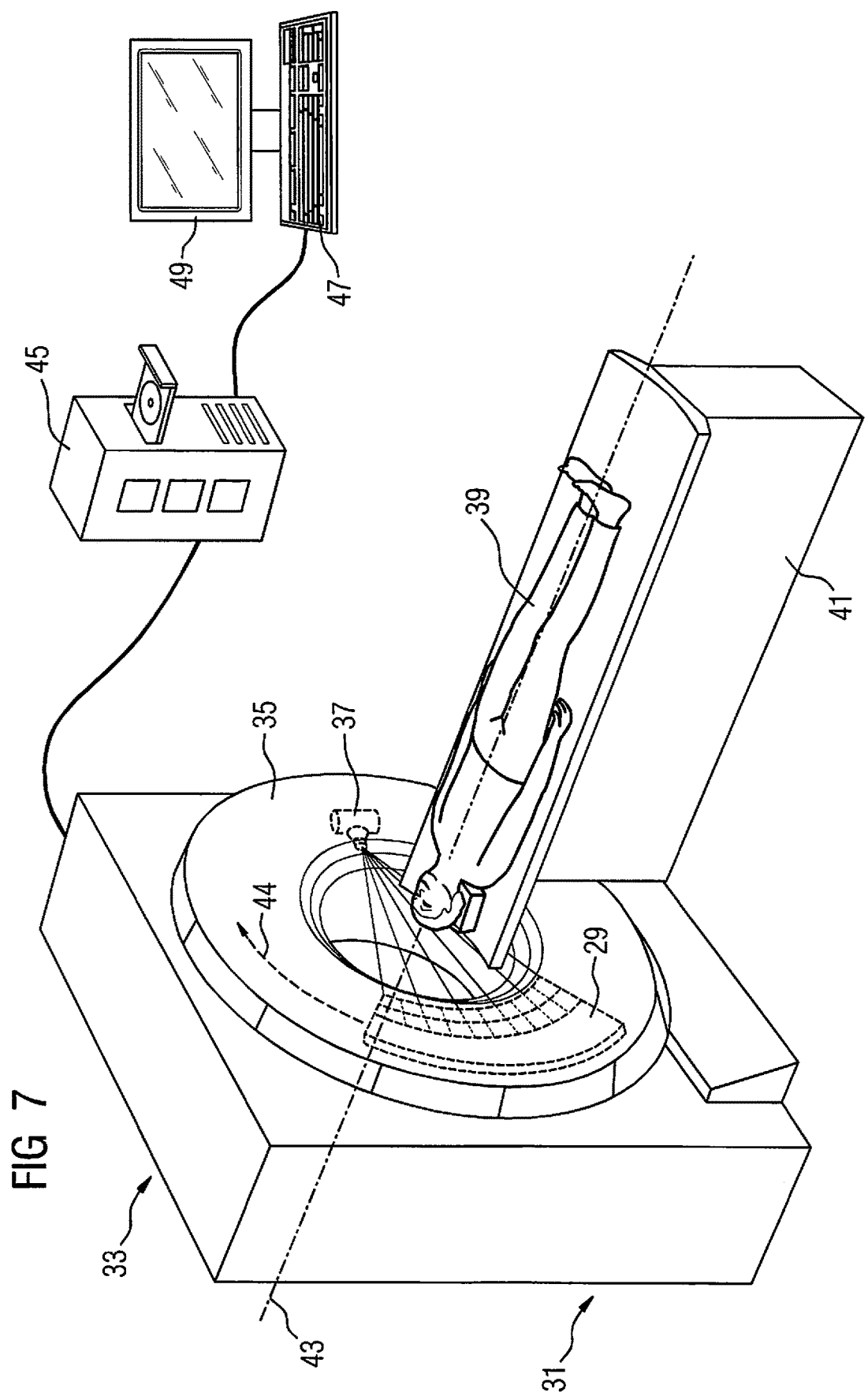
FIG. 7 shows in diagram form a concept for a computer tomography unit according to an embodiment of the invention.

FIG. 7 shows an example of an embodiment of the computer tomography unit 31 according to the invention with a detector apparatus 29. The detector apparatus 29 comprises the X-ray detector according to the invention and/or the detector group according to the invention. The computer tomography 31 contains a gantry 33 with a rotor 35. The rotor 35 includes an X-ray source 37 and the detector apparatus 29 according to the invention. The patient 39 is positioned on the patient couch 41 and can be moved along the axis of rotation z 43 by the gantry 33. The first direction phi 44 runs along the rotation direction of the rotor perpendicular to the axis of rotation z. To control and calculate the sectional images, a system computation unit 45 is used. An input device 47 and an output device 49 are connected to the system computation unit 45.

Although the invention has been illustrated in greater detail by the preferred embodiment, the invention is not restricted to the examples disclosed, and other variants can be derived therefrom by a person skilled in the art, without going beyond the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An X-ray detector, comprising:
a detection unit to convert X-rays into signal values;
a serialization unit to at least one of serialize and sort the signal values; and
an evaluation unit, the detection unit and the evaluation unit being configured in a common component, an extent of the common component along a first direction being not greater than an extent of the detection unit, wherein the evaluation unit includes
at least one correction unit to correct the signal values,
a computation unit to control the corrected signal values, and
a memory unit that stores an aging history or a radiation history of the X-ray detector and at least one correction parameter for correcting aging or irradiance of the X-ray detector,
and wherein the evaluation unit is designed such that the signal values are corrected as a function of the at least one correction parameter.

2. The X-ray detector of claim 1, wherein the at least one correction unit includes an aging correction unit and at least one of an offset-correction unit, a gain correction unit, a drift correction unit, a linearity correction unit or a fault correction unit.

3. The X-ray detector of claim 1, further comprising:
a determination unit to determine irradiance of the X-rays or signal values.

4. A detector group, comprising:
a plurality of X-ray detectors, including the X-ray detector of claim 1.

5. The detector group of claim 4, further comprising:
a detector group control to control the plurality of X-ray detectors, to data compress the signal values or to correct the signal values.

6. The detector group of claim 5, further comprising:
a group gain correction unit, a group drift correction unit, a group aging correction unit, a group linearity correction unit, a group fault correction unit or a group determination unit to determine an irradiance of the X-rays or signal values.

7. A detector apparatus, comprising:
a plurality of detector groups, including the detector group of claim 5.

8. A medical device, comprising the detector apparatus of claim 7.

9. The detector group of claim 4, further comprising:
a group gain correction unit, a group drift correction unit, a group aging correction unit, a group linearity correction unit, a group fault correction unit or a group determination unit to determine an irradiance of the X-rays or signal values.

10. The detector group of claim 4, further comprising:
a communications apparatus between at least two of the plurality of X-ray detectors of the detector group.

11. A detector apparatus, comprising:
a plurality of detector groups, including the detector group of claim 4.

12. A medical device, comprising the detector apparatus of claim 11.

13. A method, comprising:
acquiring signal values using the detection unit of the X-ray detector of claim 1;
offset correction of the signal values in the X-ray detector via an offset-correction unit, the computation unit, and the memory unit; and
serializing, via the serialization unit of the X-ray detector, the signal values.

14. The method of claim 13, further comprising:
aging correcting the signal values via an aging correction unit, and at least one of
gain correcting the signal values via a gain correction unit,
drift correcting the signal values via a drift correction unit,
linearity correcting the signal values via a linearity correction unit, and
fault correcting the signal values via a fault correction unit.

15. The method of claim 13, further comprising:
determining irradiance of the X-rays or signal values.

16. A method, comprising:
acquiring signal values using a detection unit of an X-ray detector;
offset correction of the signal values in the X-ray detector via an offset-correction unit, a computation unit, and a memory unit;
correcting an aging of the X-ray detector based on the acquired signal values and a radiation history or an aging history of the X-ray detector stored in the memory unit; and
serializing, via a serialization unit of the X-ray detector, the signal values.

17. The method of claim 16, further comprising:
aging correcting the signal values via an aging correction unit, and at least one of
gain correcting the signal values via a gain correction unit,
drift correcting the signal values via a drift correction unit,
linearity correcting the signal values via a linearity correction unit, and
fault correcting the signal values via a fault correction unit.

18. The method of claim 16, further comprising:
determining irradiance of the X-rays or signal values.

* * * * *